United States Patent [19]
Pitt et al.

[11] Patent Number: 4,672,216
[45] Date of Patent: Jun. 9, 1987

[54] LIQUID QUALITY MONITOR HAVING A PLURALITY OF PHOTODIODES FOR DETECTING LIGHT SCATTERED AT VARIOUS ANGLES

[75] Inventors: Gilles D. Pitt; Brian J. Scott, both of Saffron Walden; Michael V. Verrells, Harlow, all of England; Nicholas K. Hancock, Munich, Fed. Rep. of Germany; Phillip Extance, Solihull, England

[73] Assignee: International Standard Electric Corporation, New York, N.Y.

[21] Appl. No.: 789,989

[22] Filed: Oct. 22, 1985

[30] Foreign Application Priority Data
Oct. 26, 1984 [GB] United Kingdom ............... 8427177

[51] Int. Cl.⁴ ................... G01N 15/06; G01N 21/00
[52] U.S. Cl. .................................. 250/574; 250/575; 356/343
[58] Field of Search ............... 250/574, 573, 575; 356/343, 341, 130, 131, 134

[56] References Cited

U.S. PATENT DOCUMENTS

| | | | |
|---|---|---|---|
| 3,576,558 | 4/1971 | DeVries | 356/343 |
| 3,770,351 | 11/1973 | Wyatt | 356/343 |
| 4,146,799 | 3/1979 | Pitt et al. | 356/343 |
| 4,153,837 | 5/1979 | Ross | 250/343 |
| 4,201,471 | 5/1980 | Pitt et al. | 250/574 |
| 4,221,485 | 9/1980 | Schulze | 250/574 |
| 4,265,535 | 5/1981 | Pitt | 250/574 |
| 4,265,536 | 5/1981 | Carson et al. | 356/130 |
| 4,497,577 | 2/1985 | Sato et al. | 250/574 |

Primary Examiner—David C. Nelms
Assistant Examiner—William L. Oen
Attorney, Agent, or Firm—Menotti J. Lombardi

[57] ABSTRACT

A power station boiler condensate water monitor employs a light-scatter cell for the detection of oil and/or particulates in the water. In order to determine background scatter levels, provision is made to alternatively pass clean water through the cell (FLUSH). The offset voltages obtained from the detector outputs when clean water is employed are compensated for differences in temperature between the boiler condensate water and the clean water before substraction from the detector outputs when boiler condensate water is employed. The monitor is capable of detecting oil levels of less than 2 parts per million.

9 Claims, 6 Drawing Figures

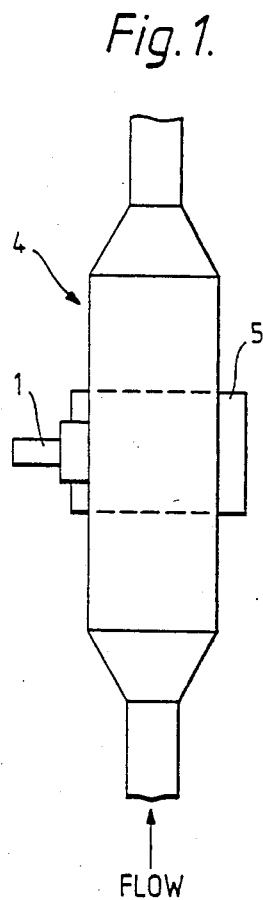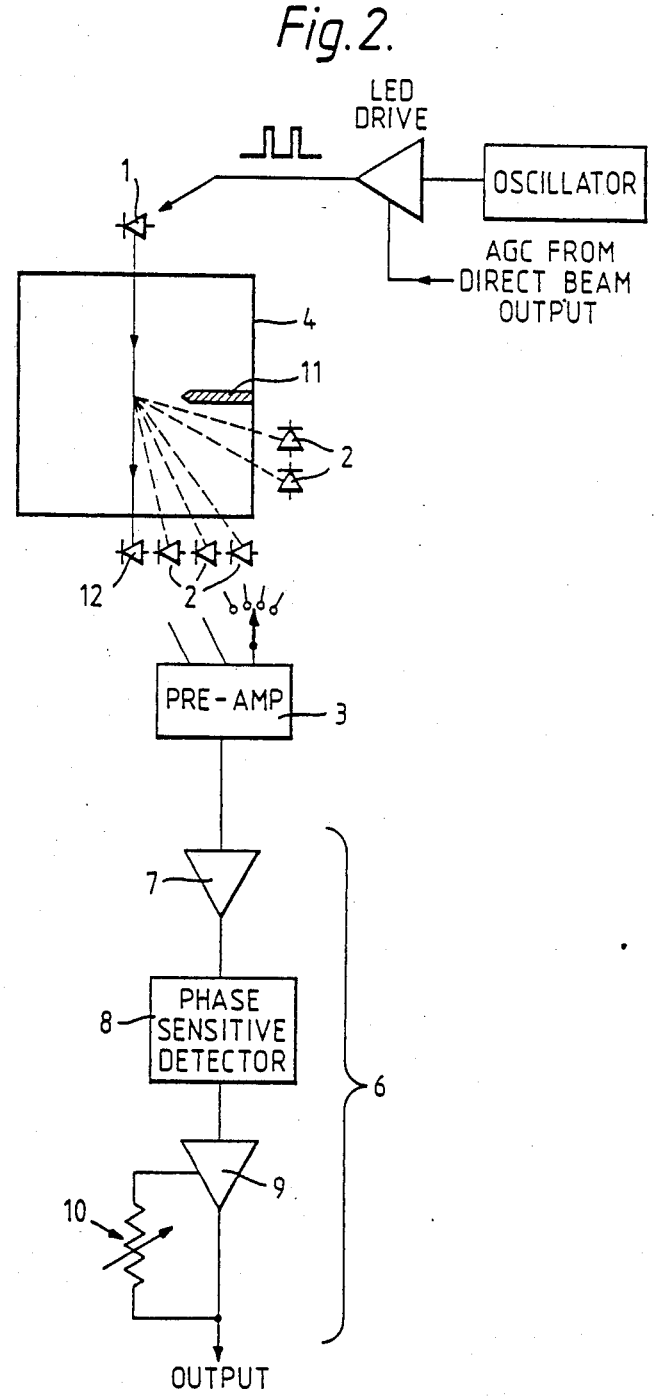

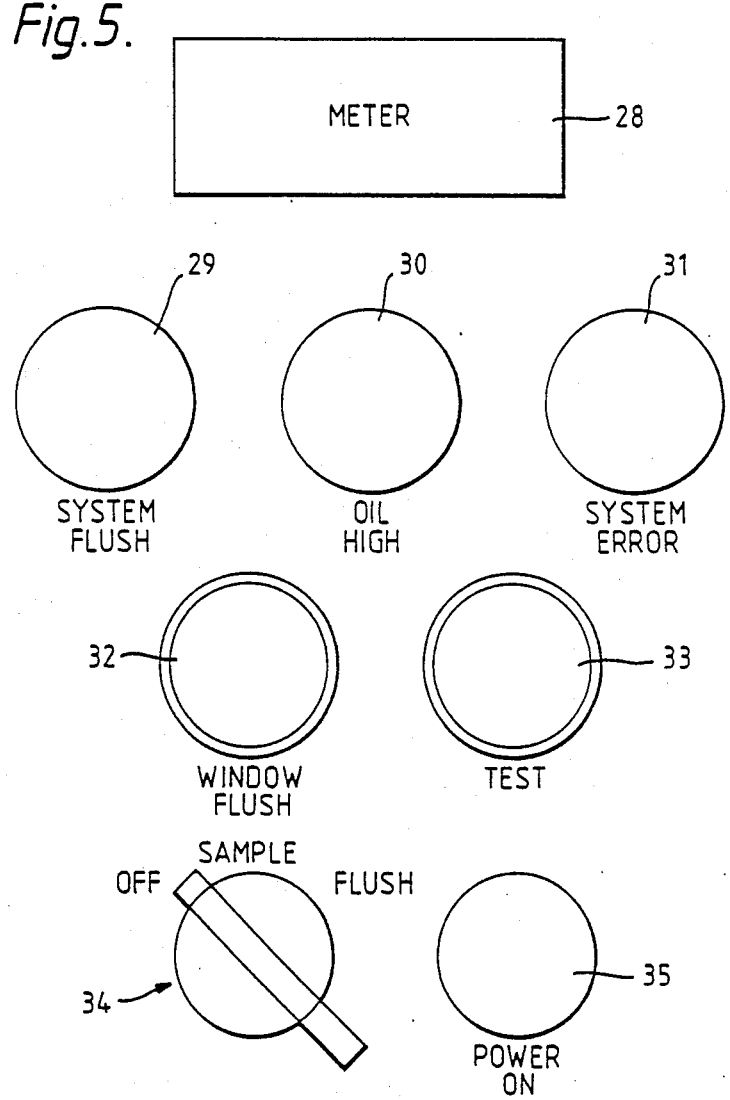
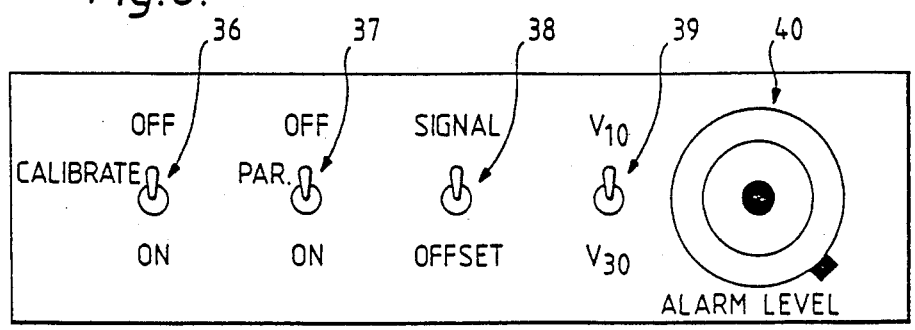

LIQUID QUALITY MONITOR HAVING A PLURALITY OF PHOTODIODES FOR DETECTING LIGHT SCATTERED AT VARIOUS ANGLES

BACKGROUND OF THE INVENTION

This invention relates to liquid quality monitors and in particular to monitors for boiler condensate water of a power station.

A major source of oil in boiler feed water is turbine lubricating oil from sealing glands. On 500 megawatt fossil fired units an oil level of 0.5 parts per million (ppm) is the maximum acceptable. High oil levels incur cost penalties by contamination of condensate polishing plant, feed-heaters and are also suspected of increasing the risk of boiler tube failure.

There are prior art systems in which there is disclosed a basic oil-in-water monitor for use with such boiler condensate water; however, the present invention is particularly concerned with a low oil concentration boiler condensate monitor, e.g. 0 to 2 ppm.

SUMMARY OF THE INVENTION

According to the present invention there is provided a liquid quality monitor comprising a cell through which the liquid to be monitored can be caused to flow, a light source coupled to one side of the cell, one or more detectors, arranged at respective angles to a light beam output from the light source and directed across the cell, to detect light scattered from contamination in the liquid to be monitored when it is caused to flow in the cell and producing corresponding detector output or outputs, respectively, means for enabling the cell to be flushed with a clean liquid, the detector output or outputs then corresponding to the background scattered light level and comprising offset voltage or voltages, respectively, means for compensating the offset voltage or voltages for difference in temperature between the liquid to be monitored and the clean liquid and processor means for calculating the contaminant level from the first mentioned detector output or outputs and the compensated offset voltage or voltages.

BRIEF DESCRIPTION OF THE DRAWINGS

Embodiments of the present invention will now be described with reference to the accompanying drawings, in which:

FIG. 1 illustrates schematically a detector cell profile;

FIG. 2 illustrates schematically a cross-section through the detector cell together with associated drive and detector circuitry;

FIG. 5 indicates a front control panel layout for the monitor, and

FIG. 6 indicates an internal switch layout for the monitor.

DESCRIPTION OF THE PREFERRED EMBODIMENTS

Figure 3:
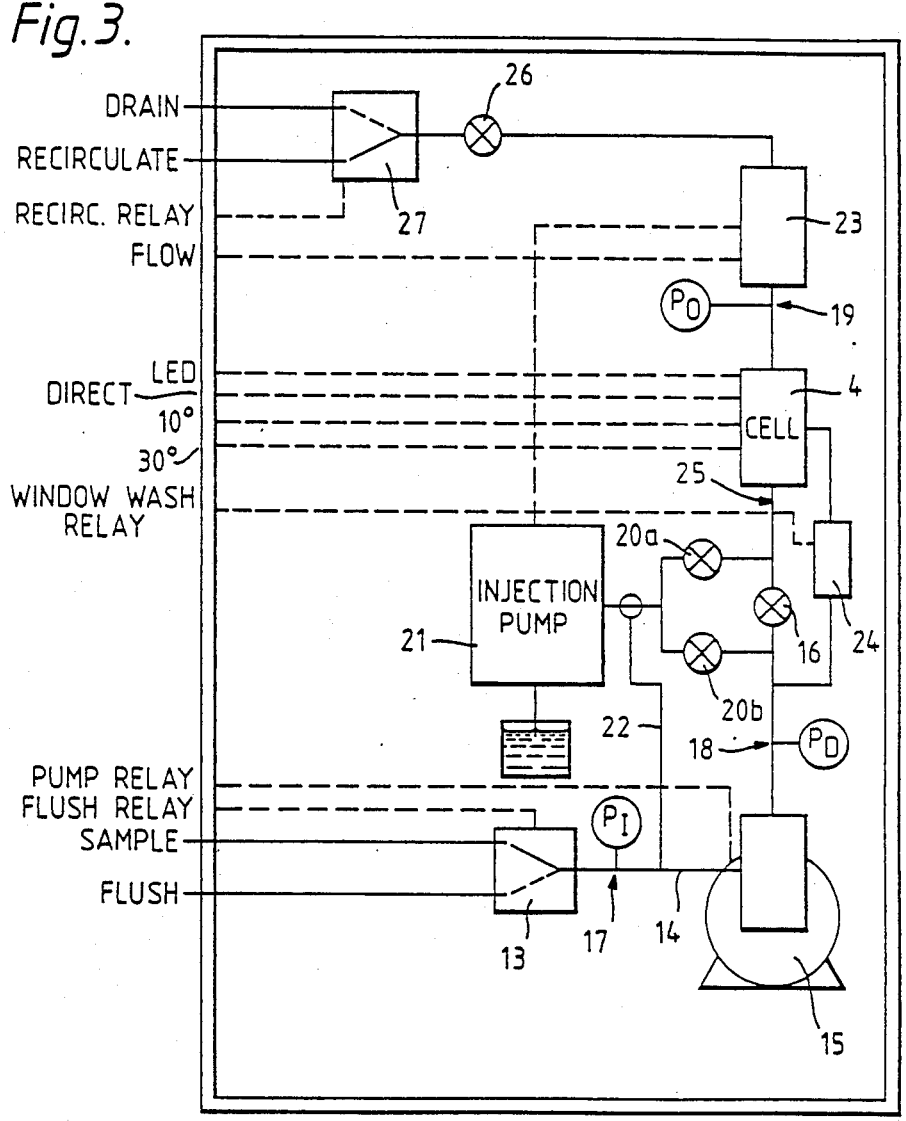
FIG. 3 illustrates schematically the plumbing layout of a monitor including a detector cell such as shown in FIGS. 1 and 2.

The monitor of the present invention employs a multi-angle scatter cell as illustrated schematically in FIGS. 1 and 2.

The monitor employs the scattering of pulsed near infra-red radiation, for example 900 nanometers, from a narrow beam light emitting diode (LED) by the oil drops in suspension. Alternatively other light sources may be employed, for example semiconductor lasers, and/or fibre optics.

As described in the above-mentioned application, the forward scattered light from an LED 1 is detected at various cell angles by photodiodes 2, each directly connected to a respective AC preamplifier 3 only one of which is indicated in FIG. 2. The preamplifiers 3 and photodiodes 2 are mounted on the cell 4 in a housing 5. Each preamplifier has a potentiometer which allows each channel gain to be adjusted during calibration. The pre-amplified photodiode signals are amplified, digitised and processed to give an oil content reading. Contributions due to particulates in the water, such as rust, may be removed or alternatively the signals may be processed for particulate content readings. Associated with each preamplifier stage 3 is a respective main amplifier stage 6 only one of which is shown comprising an amplifier 7 providing AC gain, a phase sensitive detector 8, and an amplifier 9 providing DC gain with a variable DC offset 10. The outputs are applied to processing means such as a microprocessor (not shown). Even with clean water in the cell some light scatter occurs from the walls and windows. This gives rise to an offset value which is adjusted out at 10 in the D.C. amplifier stages. A baffle 11 extends across the cell to prevent any light directly illuminating the photodiodes 2. The light transmitted directly across the cell is measured by a direct detector (photodiode) 12 and used in an automatic gain control circuit to maintain the drive for the LED 1 and thus maintain the illumination constant.

The cell 4 is incorporated in the overall monitor as illustrated in the layout of FIG. 3. The monitor is in use coupled to two water supplies, one being the water to be monitored which is coupled to the sample inlet, and the other being a clean mains supply, which is coupled to the flush inlet. The mains supply is used to flush out the monitor and provide a calibration supply. The supply is selected by an inlet solenoid valve 13 which, for example selects the flush supply when energized. The supply is coupled to the cell 4 via a line 14 including a pump 15 and a "sample input" valve 16. The pump inlet pressure $p_I$ and outlet pressure $p_D$ are monitored at 17 and 18. The cell output pressure $p_O$ is monitored at 19. Valves 20a and 20b together with valve 16 allow sample supply to be directed past an injection point where a calibrated dose of particulates, or oil, can be injected into the stream by an injection pump 21 which is such that a constant concentration of injectant is maintained independently of the bulk flow rate of the stream. The injection point can also be switched to just before the pump 15 as indicated by line 22. To facilitate constant concentration a turbine flowmeter 23 is disposed after the cell 4 and a control signal developed from the flowmeter output fed back to the injection pump for control thereof.

In order to permit the windows of the cell to be washed a window-wash system including a window wash solenoid valve 24 is incorporated in the monitor.

An orifice plate is inserted in the line to the cell at 25, that is after the line to the window-wash system. This gives a pressure drop between the water in the window-wash line and the sample stream so that, when the window wash solenoid valve is open, a stream of sample water at a higher velocity than the bulk flow is directed over the optical windows to maintain cleanliness.

A drain valve 26 is partially closed in normal operation to apply a back-pressure to the system, preventing cavitation and forcing any entrained air into solution. Air bubbles will give erroneus readings since light is scattered by them. An output solenoid valve 27 determines where the sample stream is routed, either to a drain or recirculated in the boiler condensate system or otherwise from which it was sampled. In order to prevent calibration particles being discharged into the boiler condensate system, the software may be configured so that the valve 27 selects DRAIN when the input solenoid valve 13 selects FLUSH and selects RECIRCULATE when the input valve selects SAMPLE. The valves 16, 20a and 20b and 26 are manually operated valves. The pump 15 may be a centrifugal pump and serves to provide a head for the window-wash pressure, a higher flow rate during flushes and some degree of emulsification for larger oil droplets. For example the software may be configured so that the pump is only on during "flush", "window-wash" or when the scattered light level exceeds a pre-set threshold. This latter feature may energise the pump at any time in the sampling process and is included to provide emulsification of any large oil droplets that might be present. Provided there is sufficient head to drive the sample through the monitor, the pump need not be on. If, however, the scatter signal exceeds a preset threshold, the pump is energized to provide further emulsification of the sample, increasing the signal levels in accord with the calibration. This feature increased pump lifetime and lowers sample throughput for those installations where the sample is discarded rather than restored to the recirculating system.

The monitor further includes a temperature sensor mounted close to the photodiodes which allows the offset voltages (scattered light levels with clean water or background scattered light levels) to be compensated for temperature variations. When the temperature of the flush supply (clean water) is very different to that of the sample, supply errors can arise in the computed levels of oil or particulate contamination. A software algorithm for such temperature compensation will be described hereinafter. This algorithm is such that any gain changes made during routine calibration do not necessitate change to the algorithm, which is thus independent of the pre-amplifier. This allows a factory calibration of the temperature dependence of the offset which does not need to be subsequently changed. The temperature dependence may arise from the LED, the photodetectors, or geometrical size changes of the cell itself.

Figure 4:
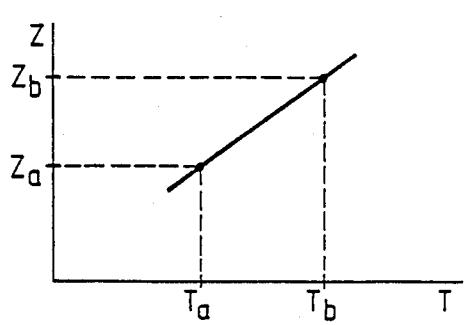
FIG. 4 is a graph showing variation of offset voltage with temperature as employed for a temperature compensation algorithm.

The derivation of the algorithm will now be described with reference to FIG. 4 which shows the linear variation of offset voltage Z (scattered light level with clean water) with the temperature T as sensed by the above mentioned temperature sensor. Defining S as the fractional change of offset with temperature, then $$S = \frac{(Z_b - Z_a)}{Z_a} \times \frac{1}{(T_b - T_a)}$$

At any temperature $T_1$, the corresponding $Z_1$ is given by $$Z_1 = Z_a(1 + S(T_1 - T_a))$$

$$Z_a = \frac{Z_1}{1 + S(T_1 - T_a)}$$

giving
At any other temperature $T_2$, the corresponding $Z_2$ is given by $$Z_2 = Z_a(1 + S(T_2 - T_a)) \quad (1)$$

$$= Z_1 \left[ \frac{1 + S(T_2 - T_a)}{1 + S(T_1 - T_a)} \right]$$

$$= Z_1 \left[ \frac{(1 = ST_a) + ST_2}{(1 - ST_a) + ST_1} \right] - Z_1 \left[ \frac{k + T_2}{k + T_1} \right]$$

where $K = \left[ \frac{1}{S} - T_a \right]$ $$= \frac{Z_1}{\left( \frac{T_1 + K}{T_2 + K} \right)}$$

Both K and S can be determined in a factory calibration, and entered into the monitor microprocessor. Thus with the flush water at $T_1$, the offset $Z_1$ at $T_1$ can be measured. Then with the sample at $T_2$, the offset $Z_2$ can be calculated from the above expression (1).

Since the temperature sensor output is of the form T=mt (°K.) with no offset, provided the potentiometer on the sensor is set to give the same output for a given T then the software can remain unchanged.

Preferably the monitor operates automatically such that with a control switch turned to "sample" it goes through a predetermined cycle which is repeated until the monitor is turned off. Any manual interruption to this cycle such as a "flush", "window-wash" or operation of a "test" switch causes the cycle to be extended for the length of the manual interruption. A one hour operating cycle may comprise a four minute flush with the clean flush water; a twenty second window wash; initial system checks (described in greater detail hereinafter); offset measurement; sampling routine, comprising continually monitoring the oil level. After thirty minutes the sampling routine may be interrupted by a twenty second window-wash. One hour after turn-on the cycle recommences with a four minute flush.

The initial flush sequence is long enough for the cell to reach temperature equilibrium with the water. The offset voltages are measured and stored together with the temperature at which they are measured. The sample water supply is automatically selected and the scatter voltages measured. The temperature of the sample water is measured to allow the offset voltages, which are subtracted from the sample voltages, to be compensated for any temperature change. The scatter voltages may be smoothed with a digital filter to reduce noise, the filter time constant being approximately one minute. The scatter signals are then input to the algorithm for calculating the oil concentration and particulate concentration therefrom. If the calculated oil level exceeds a preset alarm level then this can be used to illuminate an "oil high" warning light or to operate an alarm at a remote location.

The main signal processing/system control functions are controlled by the above mentioned microprocessor which is mounted on a main printed circuit board in a control box (not shown). On a front panel of the control box are all the controls and indicators necessary for routine operation of the monitor. Inside are further switches necessary for the calibration procedure and also a number of self-diagnostic LED error indicators. The front panel layout is shown in FIG. 5 and includes a meter 28 upon which the oil concentration can be displayed, a system error lamp 31, a window flush switch 32, a test switch 33, an off-sample-flush switch 34 and a power-on lamp 35.

In normal operation switch 34 is set to "sample" and the system continually repeats the one hour operating cycle. In the "flush" position of switch 34, the flush water input is selected either for a manual flush or for the calibration routine. Depressing the button of switch 32 turns the pump on and opens the window-wash solenoid valve. These are turned off on releasing the button. On depressing the test switch 33 all of the indicators are illuminated and the set-alarm level on the meter is displayed. This serves to check that the microprocessor is functioning correctly and that no bulbs have failed. The system flush lamp 29 is illuminated whenever "flush" is selected, whether manually or by the microprocessor. Unless in the calibration routine, when this lamp 29 is illuminated the meter reading will be zero and the scattered light levels are not measured. The oil high lamp 30 is illuminated if the meter level exceeds the level set by an internal set-alarm potentiometer. preferably the alarm has in-built hysteresis of 0.1 ppm so that the oil-high alarm will be set if, say, the level exceeds 0.5 ppm but will not be cleared until the level is below 0.4 ppm. After fifteen seconds of "oil high" a "delayed alarm relay will close to give a remote alarm signal. The lamp 30 may flash every second under certain error conditions. The system error lamp 31 is illuminated if the monitor is in condition which prevents display of the true oil content. The various causes for this and the self diagnostics associated with it are described hereinafter. Lamp 31 may also flash every second under certain error conditions. The meter 28 displays oil concentration (0-2 ppm). In the calibration mode, however, the meter can display other values. One of the above-mentioned internal switches allows display of oil or particulate concentration.

The system error lamp will light whenever an error that prevents the monitor from giving reliable readings occurs. Some situations will allow the monitor to continue if the fault clears, whereas others require attention from site personnel.

To aid the fault diagnosis seven LED's may be included on the main printed circuit. These correspond to various error conditions. Preferably the seven LED's are arranged in a horizontal row and they correspond respectively, from left to right, to preamplifier error; microprocessor fail; calibration error; direct beam fail; adc fail; $t_x$ fail; and no flow. The LED's may be off (O), on (X), or flashing (#). All seven LED's are off and the system error (SE) and oil high (OH) lamps are off when the monitor is operating normally. The SE and OH lamps may be off (O), on (X) or flashing (#).

In describing the detectable errors in the following, the status of the LED's will be shown as a 7 digit code.

In the case of no flow, that is the pulses from the flowmeter indicate that the flow is below a threshold value, for example 2 liters per min, the pump, if on, will turn off and the system error lamp will be illuminated. This indicated on the LED's as OOOOOOX. Thus the diagnostics are: OOOOOOX SE=X. If sufficient flow is re-established the error will clear and normal operation resumes.

Initial system checks are performed approximately five minutes and twenty seconds after the monitor is initially switched to sample, and every hour thereafter. In the case of an error in the pulsing circuit, that is no pulses are present to drive the transmitter LED, the system error lamp will be illuminated and the monitor will stop its cycle. The diagnostics are OOOOOOO SE=X. If the amplitude of the current pulses through the transmitter are below a present threshold, the system error lamp will light and the monitor will stop its cycle. The diagnostics are OOOOOXO SE=X. The direct beam level is normally maintained approximately constant by the automatic gain control circuit. This level may not be able to be maintained if the light output from the transmitter is too low (even at maximum drive current) or the direct beam window is excessively dirty. Should the latter be true it may be possible to clean the window by prolonged flushing. Thus if the direct beam level is too low the monitor will repeat its critical flush sequence and then the checks made so far. If the direct beam level is still too low the flush is repeated again. If the level is still low after three flushes the system error lamp will light and the monitor will stop its cycle. A symptom of this fault will thus be a prolonged flush time. The diagnostics (after the final flush only) are OOOxOOO SE=X. Following these checks the two offset voltages are measured and compared to a preset threshold. If the offset voltages are higher than this level the dynamic range of the monitor may be limited and inaccurate calibrations result. This error may occur because of excessive fouling of the scatter detector windows, a foreign body adhering to them (but not the direct beam windows) or because of a preamplifier fault. The monitor will attempt to clean the windows (to remove the errors) by performing the same routines as for direct beam level error and if this fails, the monitor will stop with the system error lamp lit. The diagnostics are XOOOOOO SE=O as soon as the error is found and XOOXOOO SE=X after three flushes fail to clear the error.

System checks are performed during the sampling routine. These comprise the flow, pulsing circuit, transmitter circuit and direct beam level checks as well as the following checks. For the preamplifier overload, if either channel is saturated the signal processing algorithm will no longer give the correct oil concentration and yet the calculated value might still be on-scale. To indicate that this is occurring, the system error lamp will flash once every second and the meter will be set to zero. If the voltages drop below saturation, the error will be cancelled and normal operation will continue. The diagnostics are #OOOOOOO SE=#. If the algorithms give "concentration" readings which are negative, the meter would give a zero reading which will be misleading. To overcome this, if a negative reading (below a preset threshold to avoid very small errors) occurs or a negative value occurs at any stage of the algorithm, the system error lamp will flash once every second. The error will be cancelled when the reading becomes positive. The diagnostics are OO#OOOOO SE=#. For a system using digital processing some means of indicating negative signals is required, since otherwise erroneous readings where negative signals are processed as "zeros" can easily occur. If the calculated oil concentration (or particulate concentration) exceeds 2 ppm the meter will read 2 ppm unless the preamplifiers are saturated. To indicate that the reading is correctly overrange the oil high and system error lights will flash once every second. The error will be cancelled when the reading comes back on scale i.e. 2 ppm. The diagnostics are OOOOOOO SE=# OH+#.

Other checks are for microprocessor failure, analogue to digital converter (ADC) failure and calibration error. If the main software loop is not being cycled, the microprocessor must not be functioning properly. A hardware circuit is used to check this. In conditions of high electrical interference this may give an erroneous state. The diagnostics are OXOOOOO. If the analogue to digital converter ceases operation there will be no scatter voltages to process. The diagnostics are OOOOXOO SE=X. A calibration error has the diagnostics OOXOOOO.

The error diagnostics are summarized in the following table:

| Error | LED | SE | OH | Automatic recovery from error |
|---|---|---|---|---|
| No flow | 000000X | X | 0 | Yes |
| Pulsing circuit | 0000000 | X | 0 | |
| Transmitter current | 00000X0 | X | 0 | |
| Direct Beam level (when flushes complete) | 000X000 | X | 0 | |
| Offset level (immediate (when flushes complete) | X000000 | 0 | 0 | |
| | X00X000 | X | 0 | |
| Preamlifier overload | #000000 | # | 0 | Yes |
| Negative readings | 00#0000 | # | 0 | Yes |
| Overrange | 0000000 | # | # | Yes |
| Microprocessor fail | 0X00000 | — | — | |
| ADC fail | 0000X00 | X | 0 | |
| Calibration error | 00X0000 | 0 | 0 | Yes |

The calibration routine will now be described. It uses the internal switches which are shown in FIG. 6. There is a calibration on-off switch 36, a use of particulate algorithm switch 37, a signal or offset switch 38, a scatter voltage switch 39 corresponding to 10° and 30° and a potentiometer 40. The potentiometer 40 allows the alarm level to be set to anywhere between 0.1 ppm and 2 ppm, for example. The switch 37 allows the signal calculated using the particulate algorithm to be displayed instead of those calculated using the oil algorithm. This is operational only when the calibration switch 36 is off and serves to check the calibration. For preamplifier gain adjustment "flush" is selected on front panel switch 34. This enables the offset levels to be measured. Any signal voltages whether offset levels or scatter signals can be measured directly at test pins on the printed circuit board. Similarly the transmitter current can also be measured. The potentiometers that adjust the gains are located in the preamplifier on the side of the scatter cell.

power can only be supplied to the injection pump 21 when front panel switch 34 is switched to "flush". This prevents possible injection of contaminants into the sample stream.

To enable a quick, low-accuracy check of the instrument calibration, the voltage levels can be displayed on the front panel meter 28 by using the internal switches. To do this the calibrate switch 36 is turned to the "on" position and the "offset" position of the signal or offset switch 38 selected. According to which channel is selected using the $V_{10}/V_+$ switch 39, the ADC input is displayed on the meter. If oil/particulates are injected, the total signal including offset is displayed. If the "signal" position is selected the meter reads the present voltage level minus the voltage level stored prior to the "offset"/"signal" switchover. If clean water was used this will be a true offset subtraction. Should the "signal" mode be selected prior to "calibrate" being turned "on", the "calibration error" LED will light since no offsets have been measured to give a meaningful substraction. (Diagnostics OOXOOOO). The offsets set in this mode are stored temporarily and are lost once "calibrate" is turned off. To ensure accuracy the instrument must be turned "off" briefly then to "sample" to restart the operating cycle and thus store the new offset levels.

We claim:

1. A liquid quality monitor for monitoring low oil concentrations in boiler condensate comprising:
   a cell through which liquid is caused to flow;
   a light source for generating a light beam, said light source positioned on one side of said cell;
   a plurality of detectors arranged at a corresponding plurality of angles with respect to a light beam from said light source, said light beam being directed across said cell, each said detector detecting light scattered from contamination within said liquid within said cell when said liquid flows in said cell, each said detector producing a corresponding detector output;
   means for flushing said cell with clean liquid, said detector output when said cell is being flushed with said clean liquid corresponding to background scattered light levels, said outputs of each of said detectors comprising a corresponding offset voltage when said cell is being flushed;
   means for amplifying and compensating said offset voltages for differences in temperature between said condensate and said clean liquid to generate corresponding temperature compensated offset voltages; and
   processor means for calculating contaminant levels based upon said detector outputs when said condensate flows through said cell and based upon said temperature compensated offset voltages corresponding to said background scattered light level, wherein said processor means measures said offset voltage of each detector at said temperature of said clean liquid used to flush said cell and wherein said temperature compensated offset voltage for said corresponding detector is calculated by said processor means according to the formula:

$$Z_2 = \frac{Z_1}{\left(\frac{T_1 + K}{T_2 + K}\right)}$$

where:
   $Z_1$ is the offset voltage at temperature $T_1$;
   $Z_2$ is the offset voltage at temperature $T_2$;

$T_1$ is the temperature of the clean liquid used to flush said cell;

$T_2$ is the temperature of the condensate; and

K is a constant stored within said processor means, whereby gain changes made during routine calibration of said means for temperature compensating and for amplifying said offset voltages do not necessitate any computational changes within said processor means.

2. The liquid quality monitor of claim 1 wherein said means for amplifying and compensating said offset voltage comprises a preamplifier and a potentiometer coupled to said preamplifier for each said detector, said preamplifier and potentiometer for use in channel gain adjustment during calibration of said liquid quality monitor, whereby said processor means calculates said temperature compensated offset voltages independently of channel gain adjustment of each preamplifier.

3. The liquid quality monitor of claim 1 wherein said processor means is further provided for diagnostic error analysis with respect to operation of said liquid quality monitor.

4. The monitor of claim 1 further comprising back pressure means hydraulically coupled downstream from said cell, said back pressure means for applying a back pressure to said liquid in said cell to prevent cavitation and to force entrained air bubbles into solution.

5. The monitor of claim 1 further comprising a pump for forcing said liquid through said cell under pressure, said pump being selectively operated, and wherein said processor means is further for generating a control signal coupled to said pump, said pump being responsive to said control signal generated by said processor means, said control signal being generated by said processor means when output signals from said detectors corresponding to a predetermined light scattering level indicates insufficient emulsification of oil within said liquid sample, said pump being turned on when said light scattering level exceeds a preset threshold thereby emulsifying said oil in said liquid.

6. A method for monitoring low oil concentration in boiler condensate comprising the steps of:

selectively flowing liquid through a cell;

transmitting light from a light source across said cell through said liquid within said cell;

sensing light transmitted across and scattered in said cell by a plurality of detectors arranged and configured about said cell at a plurality of angles to said light beam directly transmitted across said said cell; generating a detector output corresponding to each detector;

selectively flushing said cell with a clean liquid;

generating offset voltages from said plurality of detectors when said cell is flushed with said clean liquid, said offset voltage corresponding to background scattered light levels in said cell;

compensating said offset voltages for differences in temperature between said condensate and said clean liquid used to flush said cell; and computing a temperature compensated offset voltage in a processor means corresponding to said temperature of said condensate within said cell, said computed temperature compensated offset voltage being computed by said processor means according to the formula:

$$Z_2 = \frac{Z_1}{\left(\frac{T_1 + K}{T_2 + K}\right)}$$

where $Z_1$ is said temperature compensated offset voltage at temperature $T_1$;

$Z_2$ is said offset voltage of said clean liquid at temperature $T_2$;

$T_1$ is the temperature of said condensate;

$T_2$ is said temperature of said clean liquid used to flush said cell; and

K is a predetermined constant, whereby changes made during routine calibration of said monitor do not necessitate changes in said step of computing a temperature compensated offset voltage.

7. The method of claim 6 wherein said steps are organized in a plurality of subcycles, said subcycles comprising the steps of:

washing windows within said cell with a pressurized directed stream of said clean liquid;

diagnostically error checking the system operation of said monitor;

making a first offset measurement of said offset voltages; and sampling said condensate with a temperature compensated offset measurement of said offset voltages.

8. The method of claim 7 wherein said step of sampling said condensate is periodically interrupted by a step of washing said windows of said cell with a pressurized directed stream.

9. The method of claim 8 comprising the step of periodically repeating each of said foregoing steps in sequence, whereby low oil concentrations can be detected.

* * * * *